US006266550B1

(12) United States Patent
Selmon et al.

(10) Patent No.: US 6,266,550 B1
(45) Date of Patent: Jul. 24, 2001

(54) CATHETER APPARATUS FOR TREATING ARTERIAL OCCLUSIONS

(75) Inventors: Matthew R. Selmon, Woodside; James W. Vetter; Tomoaki Hinohara, both of Portola Valley; Charles F. Milo, Union City, all of CA (US)

(73) Assignee: LuMend, Inc., Redwood City, CA (US)

( * ) Notice: Subject to any disclaimer, the term of this patent is extended or adjusted under 35 U.S.C. 154(b) by 0 days.

(21) Appl. No.: 09/483,173

(22) Filed: Jan. 13, 2000

Related U.S. Application Data

(62) Division of application No. 09/008,033, filed on Jan. 16, 1998, now Pat. No. 6,157,852.

(51) Int. Cl.⁷ .................................................. A61B 17/32
(52) U.S. Cl. .......................... 600/407; 600/471; 606/190
(58) Field of Search .................................. 600/407, 137, 600/146, 104, 585, 439, 462, 464, 467, 471, 478; 606/159, 190

(56) References Cited

U.S. PATENT DOCUMENTS

| | | | |
|---|---|---|---|
| 3,640,270 | 2/1972 | Hoffmann | 128/2.1 E |
| 4,355,643 | 10/1982 | Laughlin et al. | 128/663 |
| 4,447,227 | 5/1984 | Kotsanis | 604/95 |
| 4,541,433 | 9/1985 | Baudino | 128/668 |
| 4,631,052 | 12/1986 | Kensey | 604/22 |
| 4,648,402 | 3/1987 | Santos | 128/345 |
| 4,698,057 | 10/1987 | Joishy | 604/176 |
| 5,000,185 | 3/1991 | Yock | 128/662.03 |
| 5,001,556 | 3/1991 | Nakamura et al. | 358/98 |
| 5,019,040 | 5/1991 | Itaoka et al. | 604/95 |
| 5,085,221 | 2/1992 | Ingebrigtsen | 128/660.1 |
| 5,099,845 | 3/1992 | Besz et al. | 128/653.1 |
| 5,099,850 | 3/1992 | Matsui et al. | 128/662.06 |
| 5,102,390 | 4/1992 | Crittenden et al. | 604/96 |
| 5,109,867 | 5/1992 | Twyford, Jr. | 128/772 |
| 5,114,414 | 5/1992 | Buchbinder | 604/95 |
| 5,125,410 | 6/1992 | Misono et al. | 128/662.06 |
| 5,158,564 | 10/1992 | Schnepp-Pesch et al. | 606/159 |
| 5,181,514 | 1/1993 | Solomon et al. | 128/660.09 |
| 5,193,546 | 3/1993 | Shaknovich | 128/662.06 |
| 5,203,338 | 4/1993 | Jang | 128/662.06 |
| 5,247,938 | 9/1993 | Silverstein et al. | 128/662.03 |
| 5,256,141 | 10/1993 | Gencheff et al. | 604/53 |
| 5,279,565 | 1/1994 | Klein et al. | 604/105 |
| 5,306,244 | 4/1994 | Shiber | 604/53 |
| 5,321,501 | 6/1994 | Swanson et al. | 356/345 |
| 5,325,845 | 7/1994 | Adair | 128/4 |
| 5,325,860 | 7/1994 | Seward et al. | 128/662.06 |
| 5,336,252 | 8/1994 | Cohen | 607/119 |

(List continued on next page.)

FOREIGN PATENT DOCUMENTS

| | | | |
|---|---|---|---|
| 2945237 | 5/1981 | (DE) | A61B/17/22 |
| 4429117 | 2/1996 | (DE) | A61M/29/00 |
| 0117519 | 9/1984 | (EP) | A61B/17/22 |

(List continued on next page.)

*Primary Examiner*—Marvin M. Lateef
*Assistant Examiner*—Shawna J Shaw
(74) *Attorney, Agent, or Firm*—Wilson Sonsini Goodrich & Rosati

(57) ABSTRACT

An apparatus is described for treating arterial occlusions combining an intraluminally operable catheter, having an occlusion-crossing working element, with a micro-invasive extraluminally operable locator for imaging the progress of the working element through the occlusion. Conical, abrasive, blunt-dissecting, and sharp-pointed, and steering and non-steering working elements including guide wires are described. Acoustic transducers and a flexible imaging tube are described for the locator. A suction cup is described for removably anchoring the imaging tube to a surface. A signal-emitting working element and cooperating signal-receiving locator are described. A method for treating arterial occlusions is described.

10 Claims, 7 Drawing Sheets

U.S. PATENT DOCUMENTS

| | | | |
|---|---|---|---|
| 5,350,377 | 9/1994 | Winston et al. | 606/15 |
| 5,361,768 * | 11/1994 | Webler et al. . | |
| 5,383,467 | 1/1995 | Auer et al. | 128/664 |
| 5,386,828 | 2/1995 | Owens et al. | 128/653.1 |
| 5,397,301 | 3/1995 | Pflueger et al. | 604/22 |
| 5,409,453 | 4/1995 | Lundquist et al. | 604/22 |
| 5,419,767 | 5/1995 | Eggers et al. | 604/114 |
| 5,423,846 | 6/1995 | Fischell | 606/180 |
| 5,425,705 | 6/1995 | Evard et al. | 604/28 |
| 5,439,000 | 8/1995 | Gunderson et al. | 128/664 |
| 5,452,733 | 9/1995 | Sterman et al. | 128/898 |
| 5,459,570 | 10/1995 | Swanson et al. | 356/345 |
| 5,474,065 | 12/1995 | Meathrel et al. | 128/640 |
| 5,484,412 | 1/1996 | Pierpont | 604/101 |
| 5,486,170 | 1/1996 | Winston et al. | 606/16 |
| 5,501,698 | 3/1996 | Roth et al. | 606/205 |
| 5,507,295 | 4/1996 | Skidmore | 128/662.06 |
| 5,507,795 | 4/1996 | Chiang et al. | 606/167 |
| 5,531,677 | 7/1996 | Lundquist et al. | 604/22 |
| 5,549,542 | 8/1996 | Kovalcheck | 600/146 |
| 5,569,276 | 10/1996 | Jang et al. | 606/159 |
| 5,571,215 | 11/1996 | Sterman et al. | 623/66 |
| 5,573,531 | 11/1996 | Gregory | 606/14 |
| 5,607,421 | 3/1997 | Jeevanandam et al. | 606/15 |
| 5,651,378 | 7/1997 | Matheny et al. | 128/898 |
| 5,676,151 | 10/1997 | Yock | 128/662.06 |
| 5,702,368 | 12/1997 | Stevens et al. | 604/171 |
| 5,704,898 | 1/1998 | Kokish | 600/141 |
| 5,709,693 | 1/1998 | Taylor | 606/145 |
| 5,743,876 | 4/1998 | Swanson | 604/96 |
| 5,799,655 | 9/1998 | Jang et al. | 128/662.06 |
| 5,807,388 | 9/1998 | Jevanandam et al. | 606/15 |
| 5,830,222 | 11/1998 | Makower | 606/159 |
| 5,836,882 | 11/1998 | Frazin | 600/462 |
| 5,868,760 | 2/1999 | McGuckin, Jr. | 606/139 |
| 5,876,373 | 3/1999 | Giba et al. | 604/95 |
| 5,885,238 | 3/1999 | Stevens et al. | 604/4 |
| 5,968,064 | 10/1999 | Selmon et al. | 606/189 |
| 6,081,738 * | 6/2000 | Hinohara et al. | 600/407 |
| 6,120,516 * | 9/2000 | Selmon et al. | 606/159 |
| 6,139,527 * | 10/2000 | Laufer et al. | 604/114 |
| 6,157,852 * | 12/2000 | Selmon et al. | 600/407 |
| 6,165,187 * | 12/2000 | Reger | 606/159 |
| B1 4,905,698 | 10/1991 | Strohl, Jr. et al. | 128/653 R |

FOREIGN PATENT DOCUMENTS

| | | | |
|---|---|---|---|
| 0245211 | 11/1987 | (EP) | A61M/25/00 |
| 0377269 | 7/1990 | (EP) | A61M/25/01 |
| 1585065 | 1/1970 | (FR) . | |
| WO83/03188 | 9/1983 | (WO) | A61B/1/06 |
| WO91/19528 | 12/1991 | (WO) | A61M/29/00 |
| WO92/08510 | 5/1992 | (WO) | A61M/25/00 |
| WO93/18818 | 9/1993 | (WO) | A61M/37/00 |
| WO93/20882 | 10/1993 | (WO) | A61M/29/02 |
| WO95/19143 | 7/1995 | (WO) | A61B/17/22 |
| WO96/01590 | 1/1996 | (WO) | A61B/17/22 |
| WO96/16268 | 5/1996 | (WO) | F02N/15/04 |
| WO96/16483 | 5/1996 | (WO) | H03M/13/00 |
| WO97/01459 | 1/1997 | (WO) | B60R/21/16 |
| WO97/01463 | 1/1997 | (WO) | B60R/25/04 |
| WO97/01468 | 1/1997 | (WO) | B60S/1/34 |
| WO97/13463 | 4/1997 | (WO) | A61B/17/00 |
| WO97/27897 | 8/1997 | (WO) | A61M/29/00 |
| WO98/08456 | 3/1998 | (WO) | A61B/19/00 |
| WO98/16161 | 4/1998 | (WO) | A61B/17/36 |

* cited by examiner

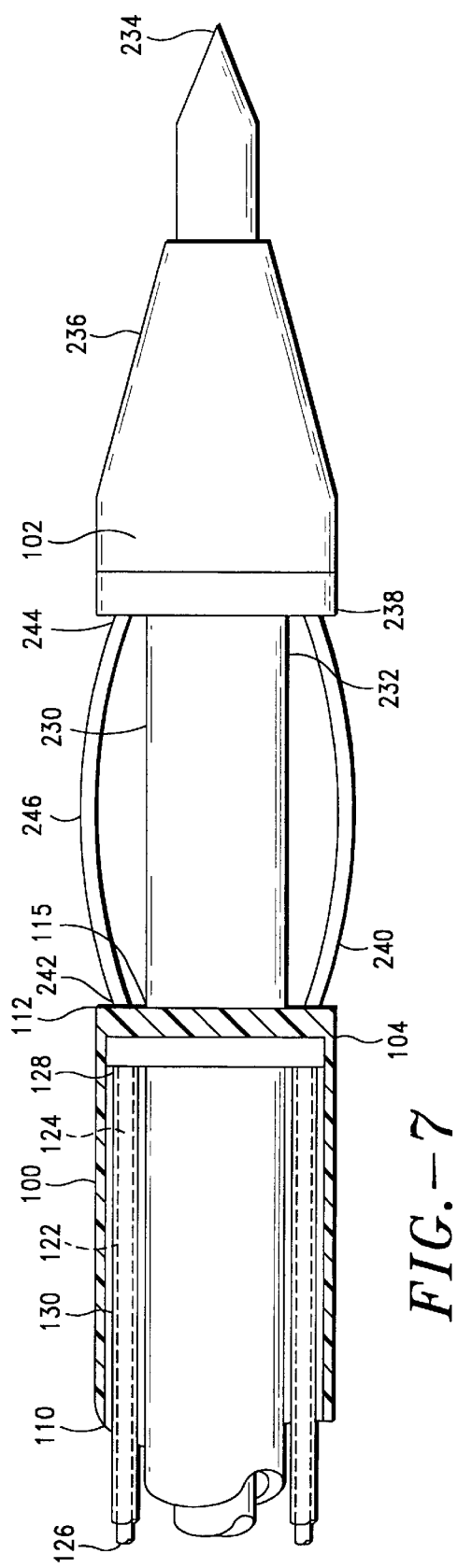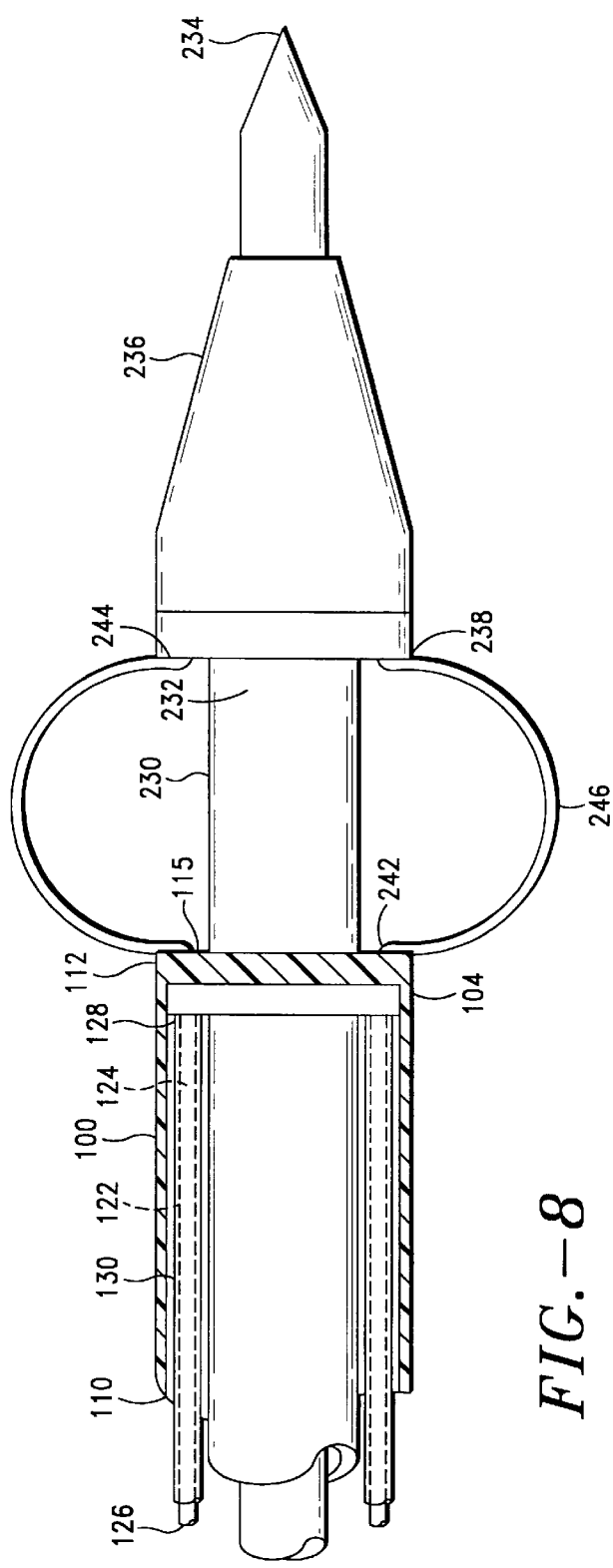

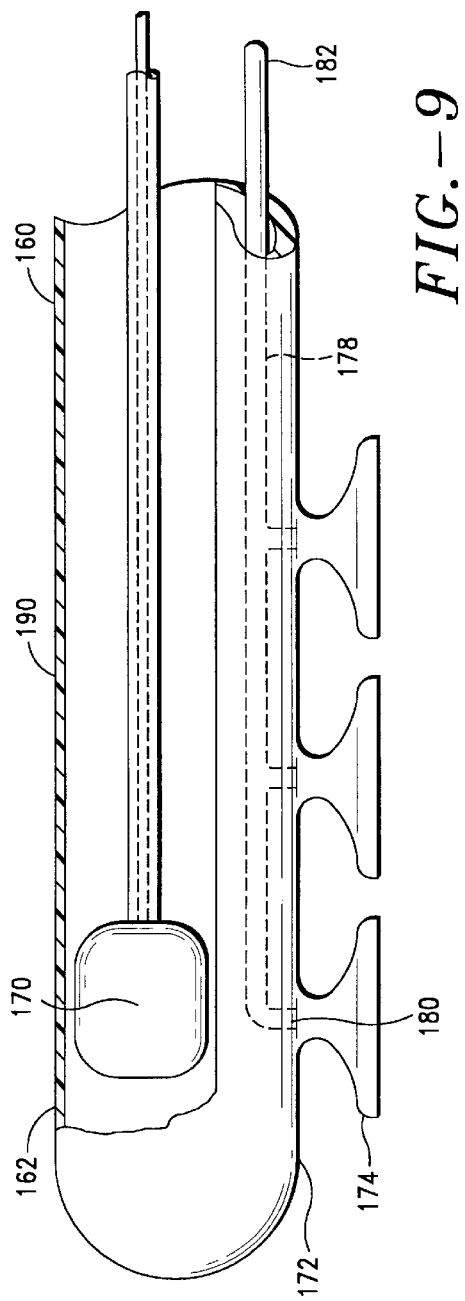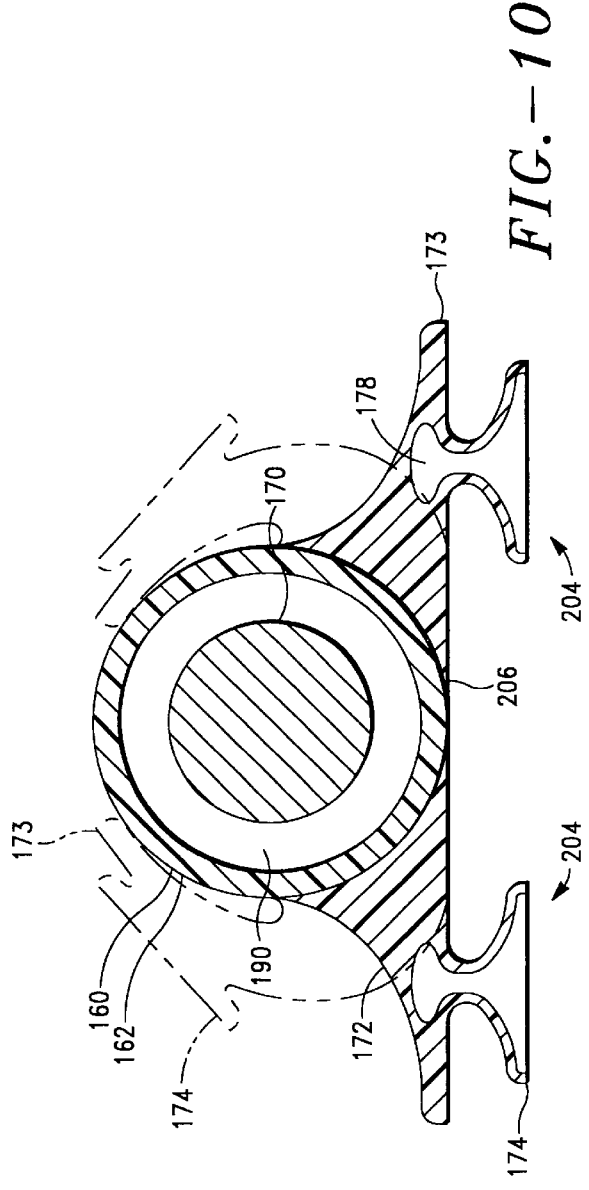

CATHETER APPARATUS FOR TREATING ARTERIAL OCCLUSIONS

RELATED APPLICATIONS

This application is a division of U.S. Patent Application No. 09/008,033, filed Jan. 16, 1998, now U.S. Pat. No. 6,157,852.

BACKGROUND OF THE INVENTION

1. Field of the Invention:

This invention relates generally to catheters and more particularly to catheter apparatus for treating arterial occlusions. The invention relates especially to the combination of an intraluminally operable atheroma-penetrating catheter device with an extraluminally operable imaging device to restore blood flow in an occluded coronary artery.

2. Background:

Atherosclerosis is a disease in which the lumen (interior passage) of an artery becomes stenosed (narrowed) or even totally occluded (blocked) by an accumulation of fibrous, fatty, or calcified tissue. Over time this tissue, known in medicine as an atheroma, hardens and blocks the artery. In the coronary arteries, which supply the heart muscle, this process leads to ischemia (deficient blood flow) of the heart muscle, angina (chest pain), and, eventually, infarction (heart attack) and death. Although drug therapies and modifications to diet and lifestyle show great promise for preventing and treating atherosclerotic vascular disease, many patients urgently require restoration of blood flow that has already been lost, especially in those having severely or totally occluded blood vessels. Unfortunately, the demand for surgical treatment of disabling and life-threatening coronary artery disease will likely increase in the decades ahead.

It has been common surgical practice to treat severe coronary artery disease by performing a coronary bypass, in which a segment of the patient's saphenous vein (taken from the leg) is grafted onto the artery at points upstream and downstream of the stenosis. The bypass often provides dramatic relief. However, this procedure involves not only dangerous open chest surgery, but also an operation on the patient's leg to obtain the segment of saphenous vein that is used for the bypass. Additionally, there is a long, often complicated and painful, convalescence before the patient is healed. Moreover, within a few years, the underlying disease may invade the bypass graft as well. The bypass can be repeated, but at ever greater peril and expense to the patient.

Fortunately, for patients with moderate stenosis, a less traumatic operation is available. A typical mechanical device for such operations is a thin, flexible, tubular device called a catheter. Through a small, conveniently located puncture, the catheter is introduced into a major artery, typically a femoral artery. Under fluoroscopic observation, the catheter is advanced and steered through the arterial system until it enters the stenosed region. At the distal (tip) end of the catheter, a balloon, cutter, or other device dilates the stenosed lumen or removes atheromatous tissue.

Cardiac catheterization procedures for treating stenoses include percutaneous transluminal coronary angioplasty (PTCA), directional coronary atherectomy (DCA), and stenting. PTCA employs a balloon to dilate the stenosis. A steerable guide wire is inserted into and through the stenosis. Next, a balloon-tipped angioplasty catheter is advanced over the guide wire to the stenosis. The balloon is inflated, separating or fracturing the atheroma. Ideally, the lumen will remain patent for a long time. Sometimes, however, it will restenose.

In directional coronary atherectomy, a catheter, containing a cutter housed in its distal end, is advanced over the guide wire into the stenosis. The housing is urged against the atheroma by the inflation of a balloon. Part of the atheroma intrudes through a window in the housing and is shaved away by the cutter.

Stenting is a procedure in which a wire or tubular framework, known as a stent, is compressed onto a balloon catheter and advanced over the guide wire to the stenosis. The balloon is inflated, expanding the stent. Ideally, the stent will hold the arterial lumen open for a prolonged period during which the lumen will remodel itself to a healthy, smooth configuration. Stents are often placed immediately following PTCA or DCA. It must be noted, however, that a severe stenosis may be untreatable by stenting, DCA, or PTCA. The catheters used in these operations are advanced to their target over a guide wire which has already crossed the stenosis. Most guide wires, however, are too slender and soft-tipped to penetrate the calcified tissue of a total occlusion. Additionally, most guide wires have a bent steering tip which is easily trapped or diverted by the complex, hard tissues often found in a severe stenosis. Without a guide wire to follow, neither PTCA nor DCA nor stenting is feasible and the interventionist may have to refer the patient to bypass surgery. Additionally, degeneration makes a saphenous vein graph a risky and therefore undesirable site of intervention.

Thus, many patients would benefit from a less traumatic alternative to bypass surgery for restoring circulation in severely stenosed or totally occluded coronary arteries. In particular, interventionists need to do what has so far been difficult or impossible: safely forge a path of low mechanical resistance through the tough, complex tissues of the severely or totally occlusive atheroma so that blood flow can be restored. Instruments have been developed which can penetrate even a total occlusion. However, such a device must make its way through the occlusion without accidentally perforating the artery. Severe dissections and cardiac tamponade can easily result when an unguided working element is diverted by the heterogeneous tissues of the occlusion. What is needed is a way of reliably guiding a working element through the atheromatous tissue. Once a path is made for a guide wire or catheter to follow, a stent can be installed or DCA or PTCA can be performed. However, reliable guidance is needed in order to open this path safely.

One guidance system used in coronary catheterization is fluoroscopy, a real-time X-ray technique which is widely used to position devices within the vascular system of a patient. For visualizing a totally occluded artery, biplane fluoroscopy can be used wherein the interventionist observes two real-time x-ray images acquired from different angles. Biplane fluoroscopy, however, is unreliable, costly and slow.

Another way of imaging the coronary arteries and surrounding tissues is intravascular ultrasound, which employs an ultrasonic transducer in the distal end of a catheter. The catheter may be equipped with an ultraminiature, very high frequency scanning ultrasonic transducer designed to be introduced into the lumen of the diseased artery. Frustratingly, however, the stenosis is often so severe that the transducer will not fit into the part that the interventionist most urgently needs to explore. Indeed, if the occlusion is too severe to be crossed by a guide wire, it may be too difficult to steer the transducer into the segment of greatest interest. Additionally, an attempt to force an imaging catheter into a severely stenosed artery may have undesirable consequences. Alternatively, the intravascular ultrasonic catheter can be placed in a vein adjacent the occluded artery. Because venous lumina are slightly broader than arterial lumina and rarely if ever stenosed, a larger transducer may be employed. Depending on its configuration, a larger transducer may acquire images over greater distances, with finer resolution, or both. However, there is not always a vein properly situated for such imaging.

While superior imaging alone is of diagnostic interest, imaging and guidance for effective intervention for severe occlusive arterial disease is what is truly desired. A reliable imaging technique is needed for discerning precisely the relative positions of a therapeutic working element, the atheromatous tissues of the occlusion and the arterial lumen proximal and distal to the occlusion as the working element is operated to cross the occlusion.

What is needed is an effective combination of a working element and an imaging system for crossing severe or total occlusions without severely dissecting the artery wall and without causing cardiac tamponade. In particular, such a combination is desired which continuously displays a stable image of the artery, the atheroma and the working element as the interventionist urges the working element through the stenosis. What is especially needed is such a combination which is deliverable and operable with minimal trauma to the patient.

SUMMARY OF THE INVENTION

It is an object of the present invention to treat arterial occlusions by minimally invasive means and, more particularly, to open a path of low mechanical resistance through the atheromatous tissues of the severely or totally occluded artery without severely dissecting the arterial wall and without causing cardiac tamponade, so that a guide wire or PTCA or DCA catheter can be placed across the occlusion.

It is an additional object of the present invention to provide a combination of an effective occlusion-crossing working element and a system for continuously displaying a stable real-time image of an artery, the arterial lumen, the atheromatous tissues therein, and the working element itself, to effectively guide the crossing element through the occlusion.

It is an additional object of the present invention to provide a combination of a catheter shaft, including a steerable intraluminally operable working element, and a locator for guiding the working element, the locator including an extraluminally operable imaging device. It is a related object of the present invention to position the locator proximate the occluded coronary artery through a small incision in the patient's chest.

It is an additional object of the present invention to provide such a combination in which the imaging device can be stabilized with respect to the surface of a beating heart while the imaging and operation are accomplished.

It is an additional object of the present invention to provide such a combination having the capability of precisely selecting the point where the working element enters the tissues of the occlusion. It is a related object of the present invention to provide such a combination with the capability of enlarging the path so opened, so that the catheter shaft itself, or other devices of diameter substantially larger than that of a mere guide wire, may be placed in that path.

In accordance with the above objects and those that will be mentioned and will become apparent below, an apparatus for treating arterial occlusions in accordance with the present invention comprises:

an elongated flexible catheter shaft having a distal end zone and an intra-arterially operable working element disposed in the distal end zone; and an extra-arterially operable locator including an imaging tube and an imaging device operatively disposed in the imaging tube, whereby the locator is positioned proximate the arterial occlusion and guides the working element for effective treatment of the occlusion.

An exemplary embodiment of the catheter apparatus according to the present invention includes a steering member including a plurality of steering wires disposed in the catheter shaft. The steering wires are fixed in the distal end zone of the catheter shaft, optionally attached to a retaining ring therein and, also optionally, confined in braided tubes for preventing mechanical interference, and are manipulable from the proximal end of the catheter shaft. The steering wires provide the apparatus of the present invention with the ability to steer the distal end of the catheter shaft, and thus the working element, by applying unequal tension to different steering wires.

Another exemplary embodiment of the catheter apparatus according to the present invention includes a plurality of rigid tubes confining the steering wires. The rigid tubes have distal ends some distance proximal to the distal ends of the steering wires, thereby increasing the flexibility of the intervening segment of the distal end zone of the catheter shaft.

Another exemplary embodiment of the catheter apparatus according to the present invention includes a working element including a pointed tissue-penetrating wire for crossing an occlusion and for penetrating arteries, veins, and interstitial tissues. This provides the apparatus of the present invention with the ability to precisely select the point of entry of the working element into the vascular, interstitial or atheromatous tissue that is to be penetrated.

Another exemplary embodiment of the catheter apparatus according to the present invention includes a working element including a rotatable motor-driven inner shaft having a tissue-penetrating point and an abrasive-coated nose cone. This provides the apparatus of the present invention with the ability to leave behind an enlarged path through an atheroma or other tissue after the working element is withdrawn.

Another exemplary embodiment of the catheter apparatus according to the present invention includes a working element including a steerable metal nose cone, disposed on the distal end of the catheter shaft, for urging the catheter shaft itself through tissues. This provides the apparatus of the present invention with the ability to leave behind an enlarged path after the working element is withdrawn and to position the catheter shaft itself in the path made by the nose cone as that path is created.

Another exemplary embodiment of the catheter apparatus according to the present invention includes a working element including a plurality of slots partially circumscribing the distal end zone of the catheter shaft. This provides the apparatus of the present invention with the ability to deflect the distal end of the catheter shaft with only a gentle force supplied by the steering member, while preserving the axial incompressibility of the catheter shaft and so its suitability for pushing the distal end against and through an occlusion.

Another exemplary embodiment of the catheter apparatus according to the present invention includes a working element including an inner shaft disposed in a lumen of the catheter shaft, a nose cone disposed on the distal end of the inner shaft, and a gap between the proximal end of the nose cone and the distal end of the catheter shaft, the gap being spanned by a pair of wires. As the catheter shaft is urged through an occlusion or other tissues and the inner shaft is forced backward into the lumen, the wires bow outward to blunt-dissect the tissues. This applies increased blunt dissecting force to the tissues as the nose cone encounters greater resistance.

Another exemplary embodiment of the catheter apparatus according to the present invention includes a working element which emits a signal, and a locator which detects the signal emitted by the working element, whereby a spatial relationship between the working element and the locator is discernible. This provides the apparatus of the present invention with the ability to readily locate the working element.

Another exemplary embodiment of the catheter apparatus according to the present invention includes an extravascularly operable imaging tube having a distal end zone defining a surface including a suction cup for adhesion to a beating heart. This provides the apparatus of the present invention with the ability to stabilize the imaging device with respect to the blood vessels and occlusion.

Another exemplary embodiment of the catheter apparatus according to the present invention includes an acoustic transducer affixed to a transducer control shaft disposed in a lumen of the imaging tube. The control shaft is mechanically manipulable by external control apparatus. The transducer is operatively coupled to external signal generating and processing apparatus for displaying an image. This provides the apparatus of the present invention with the ability to display a scanning ultrasound image of the catheter shaft, working element, occlusion, and surrounding vascular and interstitial tissues as the operation is performed.

Also in accordance with the above objects and those that will be mentioned and will become apparent below, a method for treating an arterial occlusion in a human or animal body comprises the steps of:

providing an apparatus for treating an arterial occlusion, the apparatus comprising:
an elongated flexible catheter shaft having a distal end zone and an intra-arterially operable working element disposed in the distal end zone; and
an extraluminally operable locator including an imaging tube and an imaging device operatively disposed in the imaging tube;
introducing the catheter shaft into the arterial system and placing the distal end of the catheter shaft in the lumen of a coronary artery proximate an occlusion;
introducing the locator into the chest cavity, placing the distal end of the locator adjacent the artery proximate the occlusion, and activating the locator;
operating the working element of the catheter shaft to cross the occlusion while observing the spatial relationships of the working element, the occlusion and the surrounding tissues,
whereby the locator, catheter shaft and working element are positioned proximate the occlusion and the working element is operated to cross the occlusion, while the locator reveals the anatomical location and orientation of the working element to accomplish the effective manipulation of the working element.

In an exemplary embodiment of the method according to the present invention, the catheter shaft includes a steering member and the method includes the step of operating the steering member to steer the working element when treating the occlusion.

An advantage of the present invention is that it permits the use of cardiac catheterization techniques for restoring blood flow to totally occluded coronary arteries previously inaccessible to those techniques. A related advantage is that patients can enjoy relief from cardiac ischemia while avoiding the trauma of coronary bypass surgery. Another related advantage is that the native artery can be preserved and, with it, the artery's superior blood-carrying characteristics and ability to withstand repeated intervention.

An additional advantage of the present invention is the ability to guide a penetrating element through atheromatous tissues of a totally occluded artery without perforating the arterial wall. A related advantage is that access is safely provided for a guide wire or other catheter device across a site of total occlusion.

An additional advantage of the present invention is the provision of a stable, real-time image both of the arterial anatomy and of the working element that is being guided therein, allowing accurate determination of the direction and distance from the penetrating element to a point of reentry into the natural arterial lumen beyond the occlusive lesion.

An additional advantage of the present invention is the effectively micro-invasive intra-pericardial delivery of the guidance system to the vicinity of the occlusion, requiring only a small, minimally traumatic incision in the patient's chest.

An additional advantage of the present invention is the provision of a scanning ultrasound image of the catheter shaft and its anatomical environment from an imaging device which is stabilized on the surface of a beating heart. Thus, it is easier to visualize important spatial relationships while manipulating the catheter shaft and working element.

An additional advantage of the present invention is that the working element and the distal end of the catheter shaft can be steered, the catheter shaft pushed, pulled or twisted, and the working element operated according to its particular design, all while the effect of these actions is immediately and continuously observable via the locator.

An additional advantage of the present invention is that the catheter shaft may be provided with a highly flexible distal end zone for precise maneuvering to exploit high resolution imaging available from the extravascularly operable locator.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein:

FIG. 7 is a side view of an exemplary embodiment of an apparatus according to the present invention showing a catheter shaft including a pair of blunt-dissecting wires.

FIG. 8 is a side view of an exemplary embodiment of an apparatus according to the present invention showing a catheter shaft including a pair of blunt-dissecting wires, the wires in a bowed position.

FIG. 9 is an enlarged side view of an exemplary embodiment of an apparatus according to the present invention showing a locator including a plurality of suction cups.

FIG. 10 is an enlarged sectional view of an exemplary embodiment of an apparatus according to the present invention showing a locator including a plurality of suction cups.

DETAILED DESCRIPTION OF THE INVENTION

Figure 1:
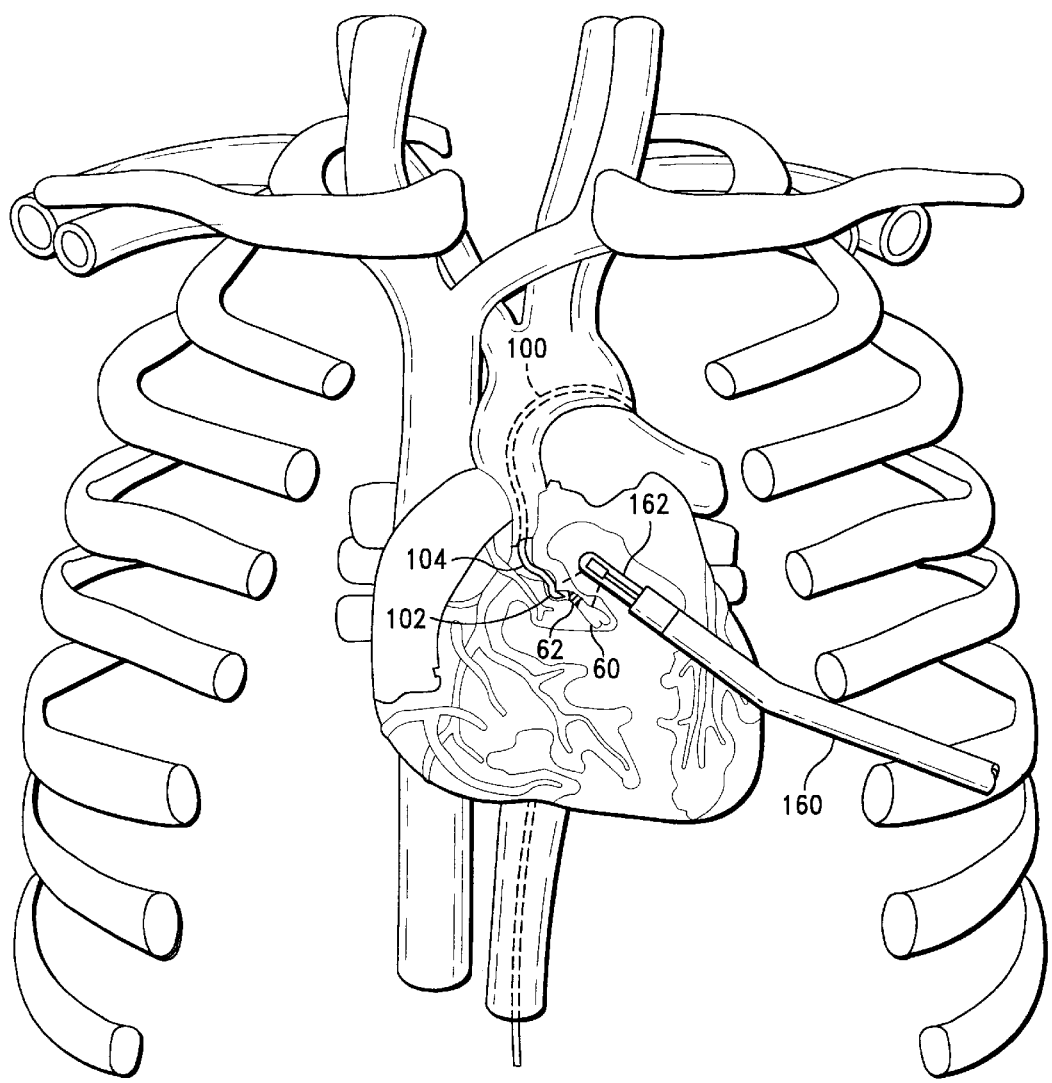
FIG. 1 illustrates an exemplary embodiment of the apparatus for treating arterial occlusions in accordance with the present invention placed proximate a total coronary artery occlusion.

The invention is now described particularly with reference to a coronary artery having a severe or total occlusion. As illustrated in FIG. 1, an exemplary embodiment of an apparatus in accordance with the present invention is shown placed proximate the occlusion 62 in a coronary artery 60. The apparatus embodies a combination of two devices which cooperate to safely bypass the occlusion 62. The first device is an intraluminally operable catheter shaft 100 including a distal end zone 104 having a working element 102 for bypassing the occlusion 62. The second device of the combination is an extraluminally operable locator 160 for locating the working element 102 with respect to the arterial lumen, the arterial wall and the tissues and boundaries of the occlusion 62. The locator 160 includes an imaging tube 162 which is introduced through a small incision (not shown) in the patient's chest and is positioned in the chest cavity adjacent the heart and proximate the occlusion 62.

Figure 2:
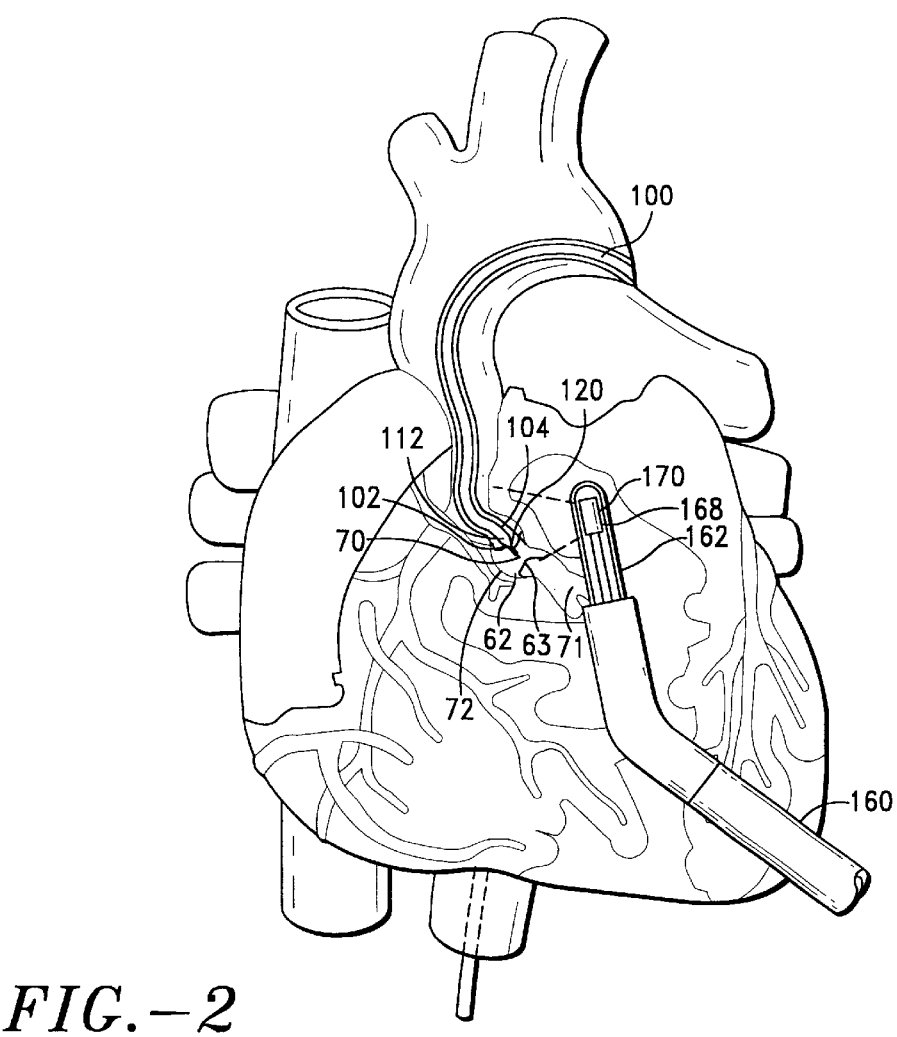
FIG. 2 is an enlarged view of the exemplary embodiment of FIG. 1 placed proximate a total arterial occlusion.

Continuing with reference to FIG. 1 and now also to FIG. 2, the imaging tube 162 is introduced through an incision (not shown) which need only be large enough to slip the imaging tube 162 into the patient's chest. The imaging tube is introduced, for example, by thoracotomy, thoracoscopy or sub-xyphoid access, is passed through a puncture in the pericardium, and is advanced until it is adjacent the surface of the heart. The external imaging instruments (not shown) of the locator 160 are then activated to display an ultrasound image.

Referring now to FIG. 2, the locator and catheter shaft are operated simultaneously to safely guide and steer the working element of the catheter shaft through the occlusion. Using standard cardiac catheterization techniques, the catheter shaft 100 is introduced through a puncture incision (not shown) into a major artery (not shown) and is advanced and guided intraluminally into an arterial branch which serves a portion of the heart. The distal end zone 104 of the catheter shaft 100 is positioned within the artery lumen and proximal to (upstream of) the total occlusion 62. The locator 160 is stabilized adjacent the heart and activated to provide an image from a vantage point close to the occluded artery 60 but outside the arterial lumen 71. It will be appreciated that because only small punctures or incisions are needed in order for the catheter shaft 100 and locator 160 to reach the operation site, the patient can expect a comfortable, uncomplicated recovery. With the present method there is no need to saw through the patient's sternum or rib cage.

Figure 3:
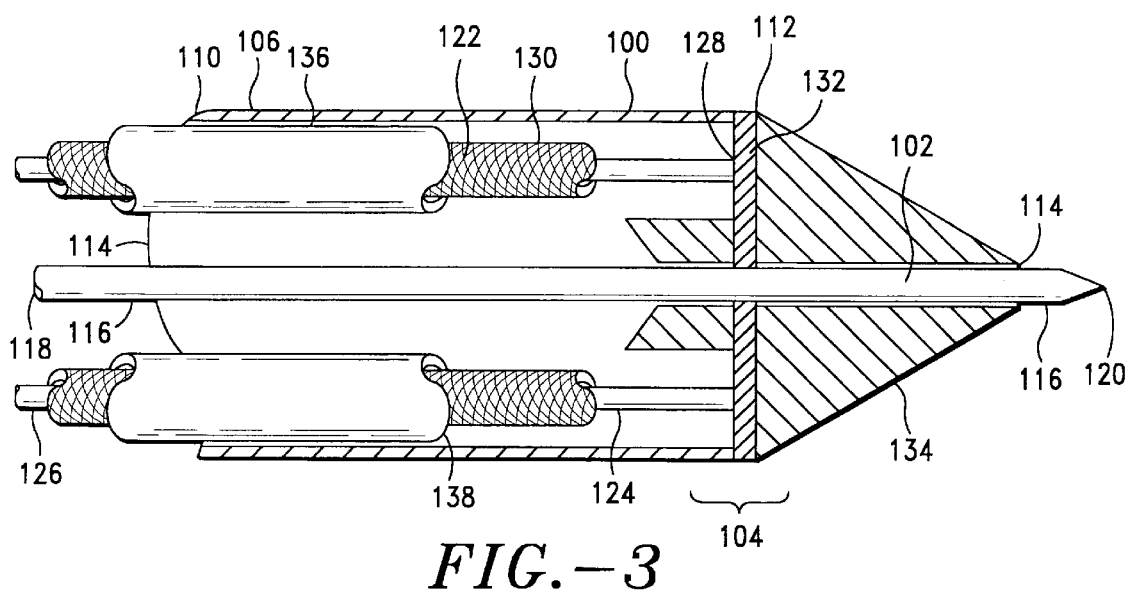
FIG. 3 is an enlarged side view of an exemplary embodiment of the apparatus showing a catheter shaft according to the present invention.

Referring now to FIGS. 2 and 3, the catheter shaft 100 and locator 160 are positionable with minimal trauma in the proximity of the occlusion 62 and are simultaneously operable to open a path through the occlusion 62. The elongated flexible catheter shaft 100 (greatly shortened in FIG. 3) includes a steerable distal end zone 104 and a working element 102 which is carried into the proximity of the occlusion 62 by the distal end zone 104. The proximal end zone (not shown) of the catheter shaft 100 is connectable to external apparatus (not shown) for manipulating the catheter shaft 100 and working element 102. The locator 160 includes an imaging tube 162 for placement of the imaging device 168 proximate the occluded artery 60. The imaging tube 162 includes a proximal end zone (not shown) connectable to external imaging instruments (not shown). The locator 160 also includes an imaging device 168 which is locatable extraluminally near the occlusion 62 and is operatively coupled to the external imaging instruments.

Referring again to FIG. 3, the catheter shaft 100 includes a proximal end 110 connectable to external apparatus (not shown), a distal end zone 104 including a distal end 112, and at least one lumen 114 therebetween. A working element 102 for penetrating tissues is disposed in the distal end zone 104. A steering member 122 is disposed in the distal end zone 104 for directing the working element 102 at and through the occlusion (not shown).

Continuing with respect to FIG. 3, the steering member 122 includes a plurality of steering wires 124 slidably disposed in the catheter shaft 100. The steering wires 124 have proximal ends 126 manipulable from the proximal end 110 of the catheter shaft 100 and distal ends 128 fixed in the distal end zone 104 of the catheter shaft 100. Optionally, braid-reinforced tubes 130 slidably confine the wires 124 to prevent the wires 124 from interfering with other parts of the catheter shaft 100. Also optionally, the steering wires 124 may be affixed to a retaining ring 132 disposed in the distal end zone 104 of the catheter shaft 100. Also optionally, rigid tubes 136 may be disposed about braid-reinforced tubes 130, the rigid tubes 136 having distal ends 138 some distance proximal to the distal ends 128 of the steering wires 124. Between the distal ends 138 of the rigid tubes 136 and the distal end 112 of the catheter shaft 100, the absence of the rigid tubes 136 increases the flexibility of the distal end zone 104 to facilitate steering.

As can be seen from FIG. 3, unequal tension on the steering wires 124 will deflect the distal end zone 104 of the catheter shaft 100 toward a wire 124 having greater tension. It can also be appreciated that, for example, the distal ends 128 of four steering wires 124 may be fixed in the distal end zone 104 of the catheter shaft 100 at ninety degree intervals about the longitudinal axis of the catheter shaft 100, with the result that the distal end 112 of the catheter shaft 100 can be deflected in two dimensions somewhat independently by manipulating the steering wires 124 in combination.

Continuing still with reference to FIG. 3, the working element 102 is steered by deflecting the distal end zone 104 of the catheter shaft 100. Because the working element 102 is carried in the distal end zone 104, the distal end zone 104 will impart to the working element 102 the deflection imparted to the distal end zone 104 by the steering member 122. In conjunction with the guidance provided by the locator 160 (discussed in detail below), this deflection enables an operator of the present invention to guide the working element 102 along a chosen path into and through the occlusion.

Although the embodiment described includes the steering member, a catheter or working element without a discrete steering member and a catheter or working element without a steering function are also within the scope and spirit of the present invention. For example, the apparatus may include a guide wire and the guide wire may include a deflected distal end which functions to steer the guide wire. Likewise, the introduction of a working element into a vascular system and the operation thereof to treat an occlusion without the specific step of steering the working element during treatment is also within the scope and spirit of the method according to the present invention.

The present invention can incorporate a wide variety of working elements. For example, a blunt-dissecting working element of the kind described in copending U.S. patent application Ser. No. 08/775,264, filed Feb. 28, 1997 now U.S. Pat. No. 5,968,064 issued Oct. 19, 1999, the entire disclosure of which is incorporated herein by reference, may be used.

Continuing with reference to FIG. 3, an exemplary embodiment of the present invention is shown in which the working element 104 includes a tissue-penetrating wire 116 disposed in a lumen 114 of the catheter shaft 100. The tissue-penetrating wire 116 includes a proximal end 118, manipulable through the proximal end 110 of the catheter shaft 100, and a sharp distal end 120 projectable from the distal end 112 of the catheter shaft 100. The tissue-penetrating wire 116 may, for example, be disposed in the lumen 114 of the catheter shaft 100 much as a trocar is disposed in a cannula. Under guidance provided by the locator 160 (discussed below), pressure is applied to the proximal end of the tissue-penetrating wire 116, urging the wire 116 into and through the occlusion as the catheter shaft 100 and steering member 122 are manipulated to direct the wire 116.

Figure 4:
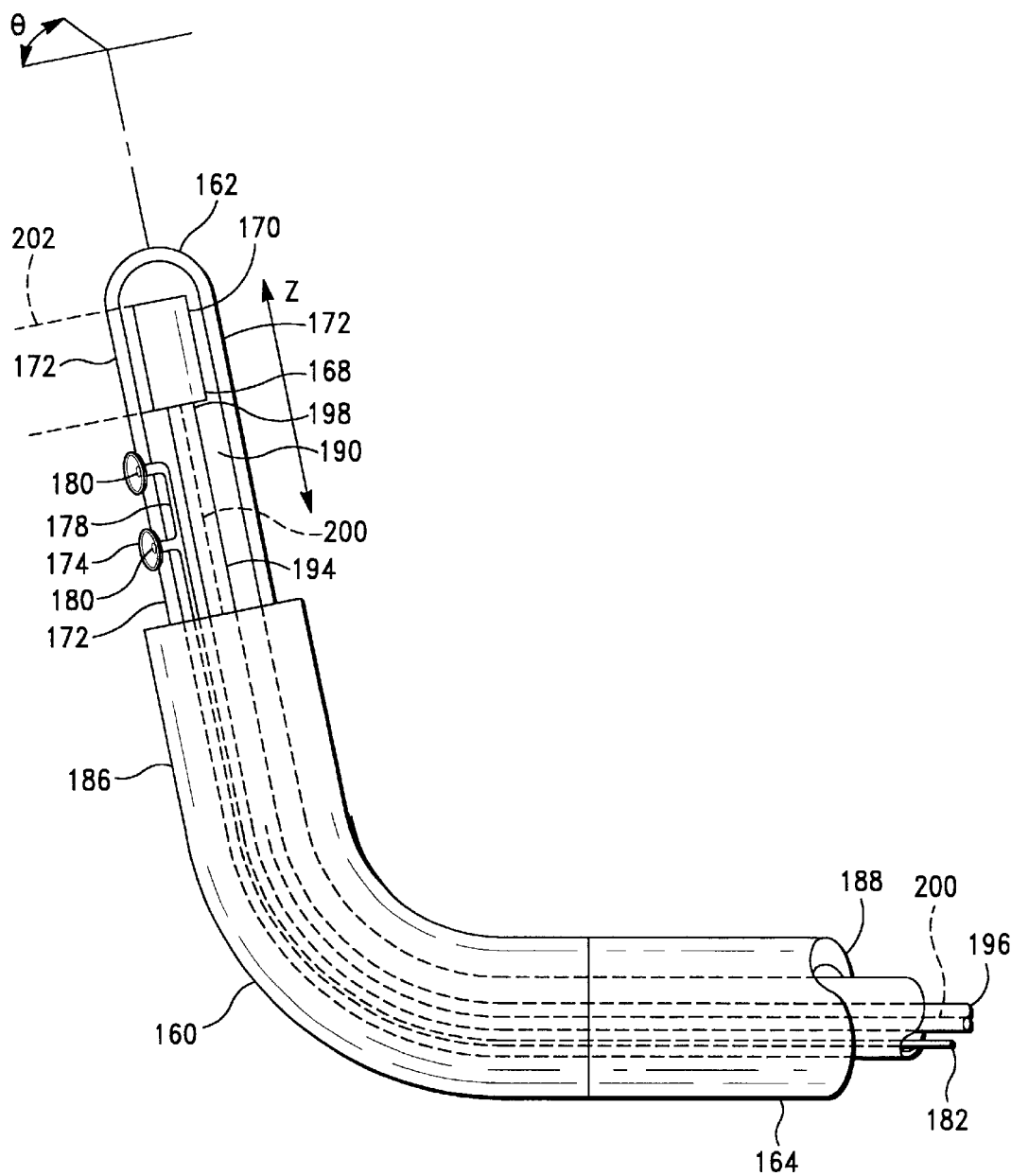
FIG. 4 is an enlarged side view of an exemplary embodiment of the apparatus showing a locator according to the present invention.

Referring again to FIG. 2 and now also to FIG. 4, the locator 160 includes an imaging device 168 (in this embodiment, an acoustic transducer 170), an imaging tube 162 for placing the imaging device 168 extraluminally proximate the occlusion 62, and one or more external imaging instruments (not shown) operatively coupled to the imaging device 168 for discerning the spatial interrelationships of the working element 102, occlusion 62, arterial lumen 71 and arterial wall 72. Optionally, the imaging tube 162 has an exterior surface 172 which forms one or more suction cups 174 for stabilizing the imaging tube 162 on a surface proximate the occluded artery 60. Also optionally, the imaging tube 162 has a suction cup activator 176 for selectively activating the suction cup 174. As illustrated in FIG. 4, the activator 176 includes a lumen 178 having a distal end 180 communicating with a suction cup 174 and a proximal end 182 communicating with a pressure-modulating device (not shown). The activator 176 may, however, encompass an aspirator, a mechanical means of activating the suction cup 174, or any other convenient way of establishing and interrupting a vacuum to temporarily stabilize a surface of the imaging tube 162 upon a surface proximate the artery 60 and occlusion 62. Generally, the suction cup may take the form of any other suction-coupling area or feature, defined by a surface 172 of the imaging tube 162, which affords adhesion to a surface.

Continuing with reference to FIG. 4, it will be appreciated that the imaging tube 162 is flexible, enabling the distal end zone 186 of the imaging tube 162 to be secured adjacent a beating heart while the proximal end zone 164 of the imaging tube 162 remains connected to external instruments (not shown) for support and control. The flexibility of the imaging tube 162 contributes to its micro-invasive quality by reducing the trauma inflicted upon tissues and by permitting the tube 162 to conform to the natural contours of bodily surfaces. As alternative ways of reducing trauma and increasing the ease of use, the imaging tube 162 may be given a shape well suited to the route of entry into the chest, or may be stabilized or flexibly supported by external apparatus at its proximal end 188.

Continuing still with reference to FIG. 4, the imaging tube 162 includes a proximal end 188, a lumen 190 originating in the proximal end 188, and a motor assembly (not shown) proximate the proximal end 188. A transducer control shaft 194, rotatably and translatably disposed in the lumen 190, includes a proximal end 196 coupled to the motor assembly (not shown), a distal end 198 coupled to the transducer 170, and a signal conducting path 200 operatively coupling the transducer 170 to the external imaging instruments (not shown). The transducer control shaft 194 is flexible enough to bend with the imaging tube 162. In this embodiment, the external imaging instruments (not shown) include an acoustic signal generator-processor (not shown) and video display device controlled by a suitably programmed general purpose computer.

Referring to FIGS. 2 and 4, the locator 160 in this exemplary embodiment provides a scanning ultrasound image of the environment of the occlusion 62. The imaging tube 162 is stabilized on the heart adjacent the artery 60 containing the occlusion 62. The motor assembly (not shown) drives the transducer control shaft 194 within the lumen 190 of the imaging tube 162 in a scanning pattern appropriate for producing an image. For example, the motor assembly (not shown) may drive the transducer control shaft 194 in a repeating reciprocating pattern while at the same time rotating the shaft. In this way, the transducer 170, which is coupled to the transducer control shaft 194, describes a two-dimensional scanning pattern which may be registered by appropriate measuring devices as combinations of a rotational angle $\theta$ and a longitudinal position Z within the imaging tube 162.

Continuing still with reference to FIGS. 2 and 4, as the transducer 170 describes the scanning pattern, the acoustic signal generator-processor (not shown) causes the transducer 170 to emit acoustic energy. A signal conducting path 200 carries an electric signal from the external instruments (not shown) (which include, in this illustration, a signal generator-processor, also not shown) to the transducer 170, which may include a piezoelectric crystal or other device for producing acoustic energy. This acoustic energy is of the type referred to as ultrasonic or ultrasound, although these terms may encompass a variety of acoustical signals embodying a variety of frequencies. The energy passes through the surface 172 of the imaging tube 162 and into the occluded artery 60 and surrounding tissues. The transducer 170 and acoustic signal are configured such that the energy is emitted in a narrowly focused beam 202 in a known direction (at a known value of the angle $\theta$) from a known position (at a known value of Z) with respect to the imaging tube 162. The transducer 107 also functions as a similarly directional acoustic signal detector, converting acoustic energy reflected by features in the environment of the imaging tube 162 to a signal which is conducted back to the signal generator-processor and measured accordingly. As are the emitted signals, the detected signals are associated with values of $\theta$ and Z.

Continuing still with reference to FIGS. 2 and 4, a third dimension, which shall be referred to as depth or as radius from the transducer 170 and given the letter r, is computable as a function of the time elapsed between the emission of a given signal by the transducer 170 and the detection of the echo of that signal. The value detected at any given time is a function of the intensity of the echo. With appropriate signal processing, this intensity can be reported via suitable video equipment as a two or three dimensional image of the environment of the imaging tube 162. General purpose computers are programmable to accomplish this function. U.S. Pat. No. 4,794,931, the disclosure of which is incorporated herein by reference in its entirety, describes a computer and instrument system implementing such a function.

Alternatively, a rotating or translating scanning transducer may be supplanted by an array of directional transducers (not shown), a phased array of transducers (not shown) or other appropriately energized and interrogated set of transducers operatively connected to the external signal generator-processor for displaying the desired image.

Referring to FIGS. 2, 3, and 4, the locator 160 provides an image of nearby anatomical features so that the position of the locator 160 with respect to the arterial wall 72 and lumen 71 and occlusion 62 is ascertained. The locator 160 is manipulated until its position is ideal for imaging the penetration of the occlusion 62. The locator 160 is then stabilized. Optionally, the imaging tube 162 includes an exterior surface 172 having one or more suction cups 174 for stabilizing the imaging tube 162 on tissues near the occluded artery 60. With the locator 160 positioned and functioning, the positions of the distal end 112 of the catheter shaft 100 and the distal end 120 of the working element 102 are ascertained. The contours of the occlusion 62 and the artery 60, as revealed by the locator 160, are also evaluated.

Continuing with reference to FIGS. 2, 3 and 4, it is seen that the catheter shaft 100 and locator 160 are placed proximate the occlusion 62. With the locator 160 positioned and functioning, the catheter shaft 100 and steering member 122 are manipulated to direct the working element 102 and the catheter shaft 100 at a point of entry (not shown) into the occlusion 62. The point of entry will have been identified in the image provided by the locator 160. The image provided by the locator 160 is also studied to plan an appropriate path through the occlusion 62. The working element 102 is then steered and advanced along that planned path under continuous observation via the locator 160. While control of the working element 102 and catheter shaft 100 is maintained via the steering member, the working element 102 and catheter shaft 100 are urged and steered though the occlusion 62 until the working element 102 is observed to re-emerge from the occlusion 62 into the arterial lumen 71.

Continuing with reference to FIGS. 2, 3 and 4, as the working element 102 and catheter shaft 100 are advanced, their positions with respect to the occlusion 62 and arterial wall 72 are carefully noted from the image provided by the locator 160. The steering member 122 is manipulated to direct the working element 102 away from any contact perceived as likely to perforate or severely dissect the artery 60. When the distal end 120 of the working element 102 reaches the distal boundary 63 of the occlusion 62, a path will have been created through the occlusion 62. The interventionist may successfully cross the occlusion 62 with a guide wire and follow up with DCA or PTCA or install a stent.

Referring again to FIG. 2, it is seen that the catheter shaft 100 and the locator 160 of the present invention cooperate to enable the operator to guide the working element 102 into and through the occlusion 62 while knowing and maintaining control of the anatomical location and orientation of the catheter shaft 100 and working element 102. Thus, the occlusion 62 can be crossed while avoiding perforation, severe dissection or other unintended trauma to the artery 60. After the occlusion 62 has been crossed, the suction cups 174 may be released, the apparatus withdrawn from the patient, and the incisions closed. Importantly, the microinvasive locator 160 provides the necessary spatial information for guidance of the working element 102 while completely avoiding the gross trauma inflicted by traditional bypass operations.

Referring again to FIG. 3, an exemplary embodiment of the present invention is shown including the above-described locator 160, catheter shaft 100, lumen 114, steering member 122, and tissue-penetrating wire 116. A metal nose cone 134 is included in the distal end 112 of the catheter shaft 100 and defines a distal orifice through which the tissue-penetrating wire 116 can project from the lumen 114. As the tissue-penetrating wire 116 is urged through tissues, the catheter shaft 100 can be steered via the steering member 122 and urged into the tissues along the path made by the wire 116. As the catheter shaft 100 follows the wire 116 through the occlusion 62, the nose cone 134 reduces the resistance encountered by the catheter shaft 100. Penetration of the occlusion 62 is observed via the locator (not shown).

Referring again to FIG. 2 and now also to FIG. 5, an exemplary embodiment of the present invention is shown including the above-described locator 160, catheter shaft 100, lumen 114, steering member 122, and tissue-penetrating wire 116 (other work elements may be used, as will be described below). The distal end zone 104 of the catheter shaft 100 also includes a plurality of rings 140. The rings 140 define paths 141 for the steering wires 124 (described above) of the steering member 122.

One or more of the rings 140 may serve to anchor the distal ends 128 of the steering wires 124. The distal end zone 104 of the catheter shaft 100 also includes a plurality of slots 142 inscribed therein for increasing the steerability of the distal end zone 104.

Figure 5:
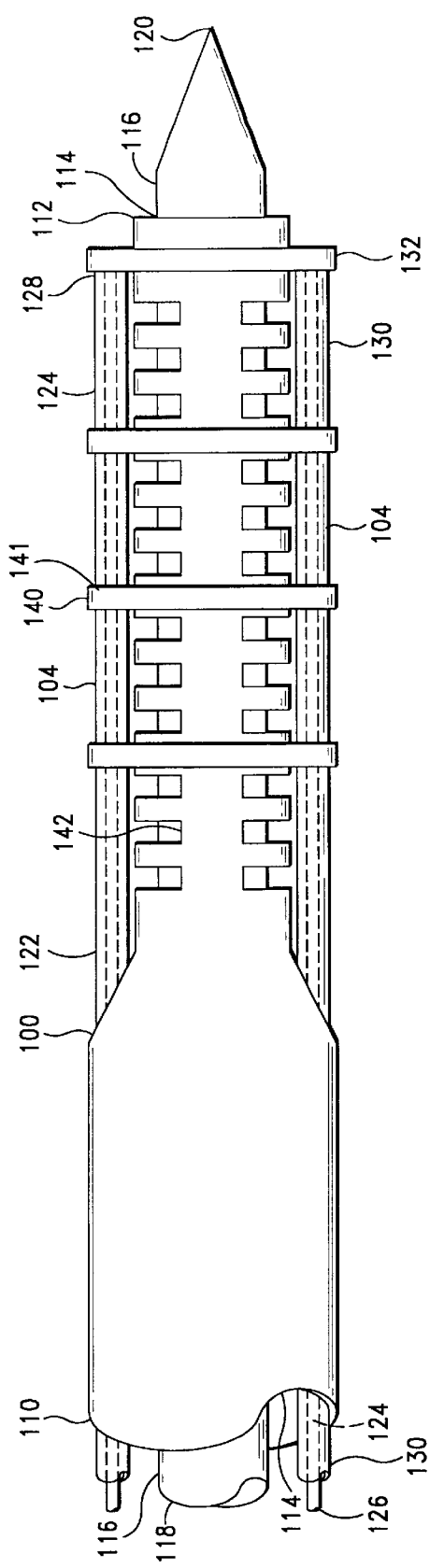
FIG. 5 is an enlarged side view of an exemplary embodiment of an apparatus according to the present invention showing a catheter shaft including rings and slots in the distal end zone of the catheter shaft.

Continuing with reference to FIG. 5, unequal tension on the steering wires 124 will deflect the distal end zone 104 and the working element 102 toward a wire having greater tension. The slots 142 in the distal end zone 104 of the catheter shaft 100 reduce the force required to compress one side of the distal end zone 104 and extend the opposite side. A steering wire 124 can thus more easily deflect the distal end zone 104. Because the slots 142 only partially circumscribe the distal end zone 104 of the catheter shaft 100, they do not appreciably reduce its axial stiffness. As a result, the distal end 112 of the catheter shaft may still be pushed firmly against a tissue surface at a point where the working element 102 is intended to enter.

Figure 6:
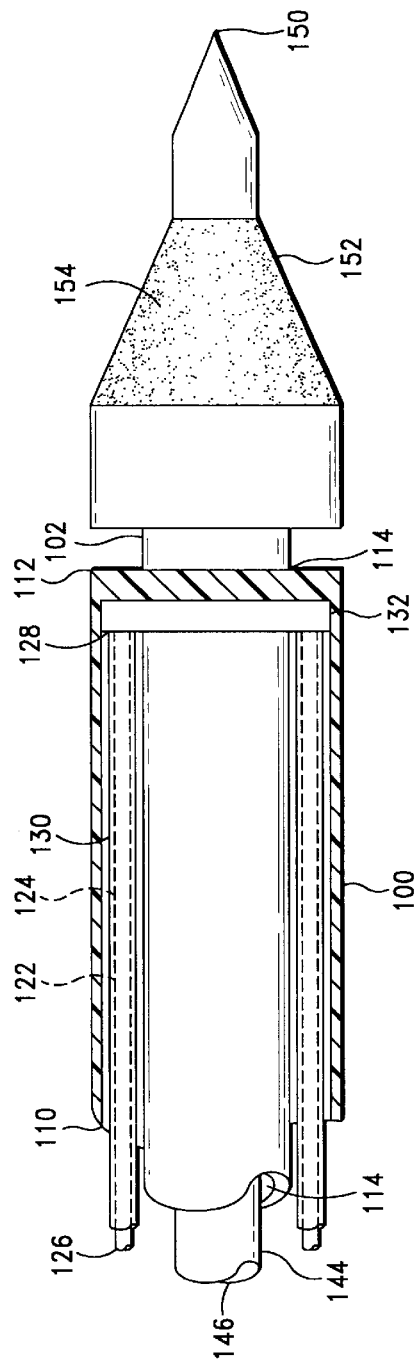
FIG. 6 is an enlarged side view of an exemplary embodiment of an apparatus according to the present invention showing a catheter shaft including a rotatable abrasive nose cone.

Referring again to FIG. 2 and now also to FIG. 6, an exemplary embodiment of the present invention is shown including the above-described locator 160, catheter shaft 100, lumen 114 and steering member 122. The working element 102 includes an inner shaft 144, rotatably disposed in the lumen 114 of the catheter shaft 100, having a proximal end 146 drivenly coupled to an external motor (not shown) proximate the proximal end 110 of the catheter shaft 100. The inner shaft 144 also includes a sharp pointed distal end 150 projecting from the distal end 112 of the catheter shaft 100, a nose cone 152 proximal to the sharp pointed distal end 150, and an abrasive coating 154 disposed on the nose cone 152 for boring into tissues.

Continuing with reference to FIG. 6, after the locator (not shown) is activated to provide an image and the steering wires 124 and catheter shaft 100 are manipulated to urge the working element 102 at a selected point of entry (not shown)

into the occlusion 62, the external drive motor (not shown) is activated, rotating the inner shaft 144 and nose cone 152. As the sharp pointed distal end 150 of the inner shaft 144 advances through the tissues (not shown), the abrasive coating 154 of the nose cone 152 grinds away tissue to open an enlarged path for the catheter shaft 100 to follow. By removing tissue, the abrasive nose cone 152 reduces the resistance of the tissues to the catheter shaft 100 and enlarges the path created through the occlusion 62.

Referring now to FIG. 7, an exemplary embodiment of the micro-invasive catheter apparatus is shown in which the catheter shaft 100 includes the above-described steering member 122, a proximal end 110, a distal end 112, a lumen 115 originating in the distal end, and a working element 102 disposed in the lumen 115. The working element 102 includes an inner shaft 230, slidably disposed in the lumen 115, having a distal end zone 232 projecting from the distal end 112 of the catheter shaft 100, a sharp pointed distal end 234 for penetrating the occlusion 62, and a nose cone 236 proximal to the sharp pointed distal end 234. The nose cone 236 has a proximal end 238. The inner shaft 230 projects from the catheter shaft 100 so that a gap exists between the distal end 112 of the catheter shaft 100 and the proximal end 238 of the nose cone 236. A plurality of dissecting wires 240 span the gap. The dissecting wires 240 have a proximal end 242 fixed in the distal end zone 104 of the catheter shaft 100, a distal end 244 fixed in the proximal end 238 of the nose cone 236, and a medial portion 246 therebetween.

Continuing with reference to FIG. 7 and now also with reference to FIG. 8, as the catheter shaft 100 is urged through an occlusion (not shown), the nose cone 236 of the inner shaft 230 will encounter resistance and the inner shaft 230 will tend to slide backward into the lumen 115. As this sliding movement narrows the gap spanned by the dissecting wires 240, the medial portion 246 of each dissecting wire 240 will be forced to bow outward. As the bowed dissecting wires 240 pass through the tissues of the occlusion (not shown), they blunt-dissect the tissues, leaving behind an enlarged passage. The greater the resistance offered by the tissue, the greater the lateral pressure exerted by the dissecting wires 240 upon the tissues.

Referring back to FIG. 2 and now particularly to FIGS. 9 and 10, an exemplary embodiment of the present invention is shown in which the imaging tube 162 of the locator 160 includes an elastomeric flared portion 173 having an exterior surface 172 defining a plurality of suction cups 174. The elastomeric flared portion 173 can be rolled around the imaging tube 162 to reduce the profile of the imaging tube 162 for insertion into the patient. The suction cups 174 are arrayed in two roughly parallel rows 204. Between the rows 204 is a region of the surface defining an imaging window 206. In the exemplary embodiment illustrated in FIG. 10, the imaging window 206 includes an acoustically transparent portion of the imaging tube 162 adjacent the lumen 190. As can be seen in FIG. 10, the transducer 170 has a view through the window 206 unobstructed by the suction cups 174 (alternatively, the imaging window 206 may be located on a portion of the surface 172 of the imaging tube 162 which also defines a single enlarged suction area). The imaging tube 162 optionally includes a suction cup activating lumen 178 having a distal end zone 180 communicating with the suction cups 174 and a proximal end 182 coupled with a pressure modulating device (not shown). The lumen 178 and pressure modulating device permit rapid, minimally traumatic temporary stabilization of the imaging tube 160 on the heart surface.

Figure 11:
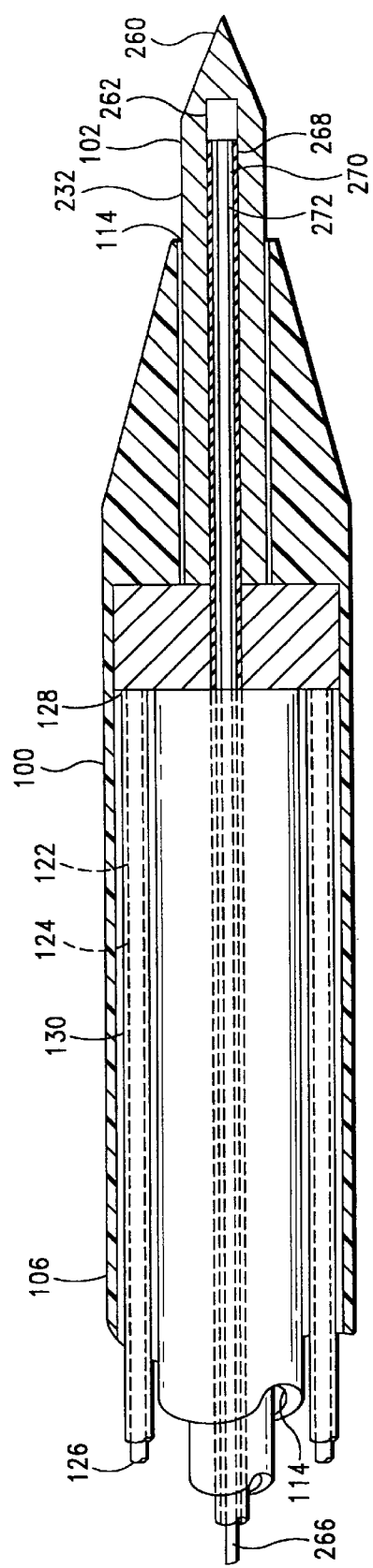
FIG. 11 is an enlarged side view of an exemplary embodiment of an apparatus according to the present invention showing the structure of a catheter shaft including a signal-emitting working element.

Referring back to FIG. 2 and now also to FIG. 11, an exemplary embodiment of the present invention is shown including the above-described locator 160, catheter shaft 100, lumen 114 and steering member 122. In this embodiment, the working element includes a tissue-penetrating working element 102 having a distal end 260. A signal emitter 262 is disposed in the distal end 260. A signal generator (not shown) is operatively coupled to the signal emitter 262. In this embodiment, the signal generator is external to the body and is coupled to the emitter through an electrically conductive path 266 originating in the proximal end zone 106 of the catheter shaft 100 and terminating at the emitter 262. As illustrated, the electrically conductive path 266 includes an outer conductor 268 disposed in the catheter shaft 100, a tubular dielectric layer 270 therein, and an inner conductor 272 disposed within the dielectric layer 270. However, any other energy-delivering or converting means can be employed to energize the emitter 262. When the locator 160 and emitter 262 are activated within the body, the locator 160 selectively detects the signal emitted by the emitter 262 in order to discern a spatial relationship between the working element 102 and the locator 160. Alternatively, the signal emitter 262 and the associated conductive path 266 may be disposed in the distal end of a guide wire (not shown).

Alternatively, the signal emitter 262 may be disposed in a working element which is essentially a guide wire, optionally steerable. Likewise, the catheter shaft may be of a simpler design than the one shown in FIG. 11; in particular, a catheter shaft without a steering member, and a signal-emitting guide wire distal end not surrounded by a separate catheter shaft, are both within the scope of the present invention.

While the foregoing detailed description has described several embodiments of the invention, it is to be understood that the above description is illustrative only and not limiting of the disclosed invention. Particularly, the imaging device need not be an acoustic transducer and need not accomplish its imaging by scanning or mechanical movement in any particular manner. The imaging device may be operatively coupled to external instruments by any appropriate mechanical, electromagnetic, optical, wave guide or other path. The image that is displayed may be computed by any of a variety of algorithms for extracting one-, two-, or three-dimensional information from energy reflected, scattered or absorbed within tissues. The imaging tube may be stabilized proximate the occlusion 62 by any appropriate mechanical, pneumatic, hydraulic or other means. Additionally, the locator 160 need not approach the heart in the particular manner described; alternative routes may be taken.

It will also be noted that, depending on the configuration and support of the working element, either the catheter shaft or the working element or both may be placed in the path created by the working element. Also, either the working element or the catheter shaft may be left in the path so created to serve as a conduit or for some other purpose. The catheter shaft may include a lumen to facilitate blood flow in the bypass. The catheter shaft or work element may include a balloon for stabilization, for interruption of flow, or for other purposes.

Likewise, the steering member may include more or fewer than the two wires illustrated in the drawing figures. The working element 102 may include any mechanical, thermal, optical, chemical or other device for penetrating tissues, treating an occlusion or delivering a medicament. The catheter shaft 100 and working element 102 may be configured such that only the working element 102 traverses certain tissues or, alternatively, the catheter shaft 100 itself may follow along with the working element 102. It will be appreciated that the embodiments discussed above and the virtually infinite embodiments that are not mentioned could easily be within the scope and spirit of the present invention. Thus, the invention is to be limited only by the claims as set forth below.

What is claimed is:

1. An apparatus for creating a path through an arterial occlusion, comprising:
   a intra-arterial catheter shaft having distal end and a proximal end and at least one lumen therethrough;
   a working element comprising;
      an inner shaft slidably disposed in a lumen of the catheter shaft having a distal end zone projecting from the distal end of the catheter shaft;
      a nose cone coupled to the distal end zone of the inner shaft; and
      a sharp, pointed distal end proximate to a distal end of the nose cone; and
   a plurality of dissecting wires wherein each dissecting wire comprises a proximal end coupled to the distal end of the catheter shaft and a distal end coupled to a proximal end of the nose cone, and a medial portion between the distal end and the proximal end, wherein each of the dissecting wires is substantially aligned with a central axis of the catheter shaft between its proximal end and its distal end, and wherein as the catheter shaft is urged through the occlusion, the nose cone contacts tissue, which slows the distal progress of the working element relative to the distal progress of the catheter shaft, causing the medial portion of each of the plurality of dissecting wires to bow outward from the central axis of the catheter shaft while maintaining the substantial alignment with the central axis of the catheter shaft such that the dissecting wires blunt dissect tissues encountered by the dissecting wires as the dissecting wires advance distally.

2. The apparatus of claim 1, further comprising an extra-arterial locator, the extra-arterial locator comprising:
   a flexible imaging tube with a distal end, a proximal end, and at least one lumen therethrough;
   an imaging device in the at least one lumen; and
   at least one attachment device on an outer surface of the flexible imaging tube between the distal end and the proximal end, wherein the extra-arterial locator is operable to be stabilized proximate to an artery containing the occlusion using the at least one attachment device, so that the imaging device may be used to aid in directing the sharp, pointed distal end and the working element to and through the occlusion.

3. The apparatus of claim 2, further comprising:
   a rotatable and translatable control shaft disposed in the lumen of the flexible imaging tube, wherein the control shaft is coupled to the imaging device at a distal end and to a motor assembly such that the imaging device may be moved in a scanning pattern to collect position data; and
   a signal conducting path coupling the imaging device to an imaging instrument, wherein the imaging instrument is controllable by a computer to produce an image from the position data.

4. The apparatus of claim 3, wherein the at least one attachment device comprises a suction cup, and wherein the apparatus further comprises a lumen having a distal end coupled to the suction cup and a proximal end coupled to a pressure modulating device operable such that a vacuum may be created to stabilize a surface of the flexible imaging tube.

5. The apparatus of claim 4, wherein the suction cup is formed as a part of an exterior surface of the flexible imaging device, and wherein the exterior surface is of an elastomeric material such that the suction cup may be manipulated into different positions proximate the flexible imaging tube to assist in insertion of the flexible imaging tube into a body.

6. The apparatus of claim 5, wherein the at least one attachment device comprise two rows, each of at least one suction cup, wherein the rows are located parallel a central axis of the flexible imaging tube, and wherein the apparatus further comprises an imaging window through the flexible imaging tube that is located between the rows, the imaging device being located proximate to the imaging window.

7. A method for treating an arterial occlusion in a mammal, comprising:
   inserting a catheter shaft and a working element into an occluded artery, wherein the working element comprises,
      an inner shaft slidably disposed in a lumen of the catheter shaft having a distal end zone projecting from the distal end of the catheter shaft;
      a nose cone coupled to the distal end zone of the inner shaft; and
      a sharp, pointed distal end proximate to a distal end of the nose cone, wherein a distal end of the catheter shaft and a proximal end of the nose cone are coupled by a plurality of flexible dissecting wires, each of the flexible wires having a medial portion between the distal end of the catheter shaft and the proximal end of the nose cone, and wherein each of the dissecting wires is substantially aligned with a central axis of the catheter shaft between the distal end of the catheter shaft and the proximal end of the nose cone;
   urging the pointed, sharp end against the occlusion such that an opening in the occlusion is created and such that a distal end of the nose cone enters the opening;
   further urging the nose cone against the occlusion, wherein as the nose cone encounters resistance, which slows the distal progress of the working element relative to the distal progress of the catheter shaft, the medial portion of each of the plurality of dissecting wires is caused to bow outward from the central axis of the catheter shaft such that the dissecting wires blunt dissect tissues encountered by the dissecting wires and widen the opening as the dissecting wires advance distally.

8. The method of claim 7, further comprising:
   positioning an extra-arterial locator proximate an occluded artery, wherein the locator comprises a flexible imaging tube and an imaging device disposed in a lumen of the flexible imaging tube;
   stabilizing the extra-arterial locator by activating an attachment device that causes the extra-arterial locator to be temporarily fixed to a body part of the mammal;
   positioning the working element against the occlusion by, manipulating the catheter shaft by applying unequal pressure to at least two steering wires attached to a proximal end of the working element; and
   manipulating an imaging device control shaft of the extra-arterial locator to rotate and translate the imaging device in a scanning pattern such that an image of an area of the occlusion may be generated.

9. The method of claim 8, wherein stabilizing the extra-arterial locator comprises operating a pressure control device coupled to suction cups on an exterior surface of the flexible imaging tube such that the suction cups adhere to the body part.

10. The method of claim 9, wherein positioning the extra-arterial locator comprises deforming the suction cups about the exterior surface of the flexible imaging tube such that positioning around body parts is facilitated.

* * * * *